(12) United States Patent
Endo et al.

(10) Patent No.: US 8,017,594 B2
(45) Date of Patent: Sep. 13, 2011

(54) AGENT AGAINST PSYCHOSOCIAL STRESSES

(75) Inventors: Kazuki Endo, Choshi (JP); Noriyuki Ashida, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 337 days.

(21) Appl. No.: 12/302,044

(22) PCT Filed: Jun. 26, 2007

(86) PCT No.: PCT/JP2007/000688
§ 371 (c)(1),
(2), (4) Date: Nov. 24, 2008

(87) PCT Pub. No.: WO2008/001495
PCT Pub. Date: Jan. 3, 2008

(65) Prior Publication Data
US 2009/0118224 A1    May 7, 2009

(30) Foreign Application Priority Data

Jun. 27, 2006   (JP) .................. 2006-177094

(51) Int. Cl.
*A01N 43/04*   (2006.01)
*A61K 31/70*   (2006.01)
(52) U.S. Cl. ................ 514/50; 514/42; 514/43; 514/49; 514/51
(58) Field of Classification Search .................. None
See application file for complete search history.

(56) References Cited

U.S. PATENT DOCUMENTS

| 2002/0028787 A1 | 3/2002 | Watkins et al. |
| 2005/0129710 A1 | 6/2005 | Renshaw et al. |
| 2005/0203053 A1 | 9/2005 | Wurtman et al. |

FOREIGN PATENT DOCUMENTS

| JP | 58 67621 | 4/1983 |
| JP | 60 136515 | 7/1985 |
| JP | 7 215879 | 8/1995 |
| JP | 10 203989 | 8/1998 |
| JP | 2002-65175 | 3/2002 |
| JP | 2003 517437 | 5/2003 |
| JP | 2003-327528 | 11/2003 |
| JP | 2005-330213 | 12/2005 |
| WO | WO 00/06174 | * 2/2000 |

OTHER PUBLICATIONS

Hidehiko Yokogoshi, et al., Proceedings of Annual Meetting of Japan Society for Bioscience, Biotechnology, and Agrochemistry 2006, Lecture No. 2J16p01-03, p. 72, with partial English translation and cover page.
Folia Pharmacologica Japonica, vol. 120, No. 4, pp. 229-236, 2002, with English Abstract.
"Mechanism of Sleep", "Stress and Sleep", Asakura Publishing Co., Ltd., 1997, pp. 52-73, with partial English Translation.

* cited by examiner

*Primary Examiner* — Patrick Lewis
(74) *Attorney, Agent, or Firm* — Oblon, Spivak, McClelland, Maier & Neustadt, L.L.P.

(57) ABSTRACT

To provide a novel anti-psychosocial stress agent which is highly safety and can be continuously taken, more particularly, a novel anti-psychosocial stress agent which prevents or alleviates psychosocial stress.
The invention provides an anti-psychosocial stress agent containing, as an active ingredient, uridylic acid, uridine, or uracil. Since uridylic acid, uridine, or uracil, which is an active ingredient of the anti-psychosocial stress agent of the present invention, is inexpensively available and is a biological component, the agent exhibits high safety and can be continuously taken. Therefore, the anti-psychosocial stress agent of the present invention is effective for mitigating, alleviating, or relieving psychosocial stress, which is an issue in modern society. When the anti-psychosocial stress agent is taken before development of symptoms associated with psychosocial stress, the symptoms can be prevented. The anti-stress effect of the agent is superior to that of GABA, which has become of interest and has been incorporated into, for example, foods.

6 Claims, 2 Drawing Sheets

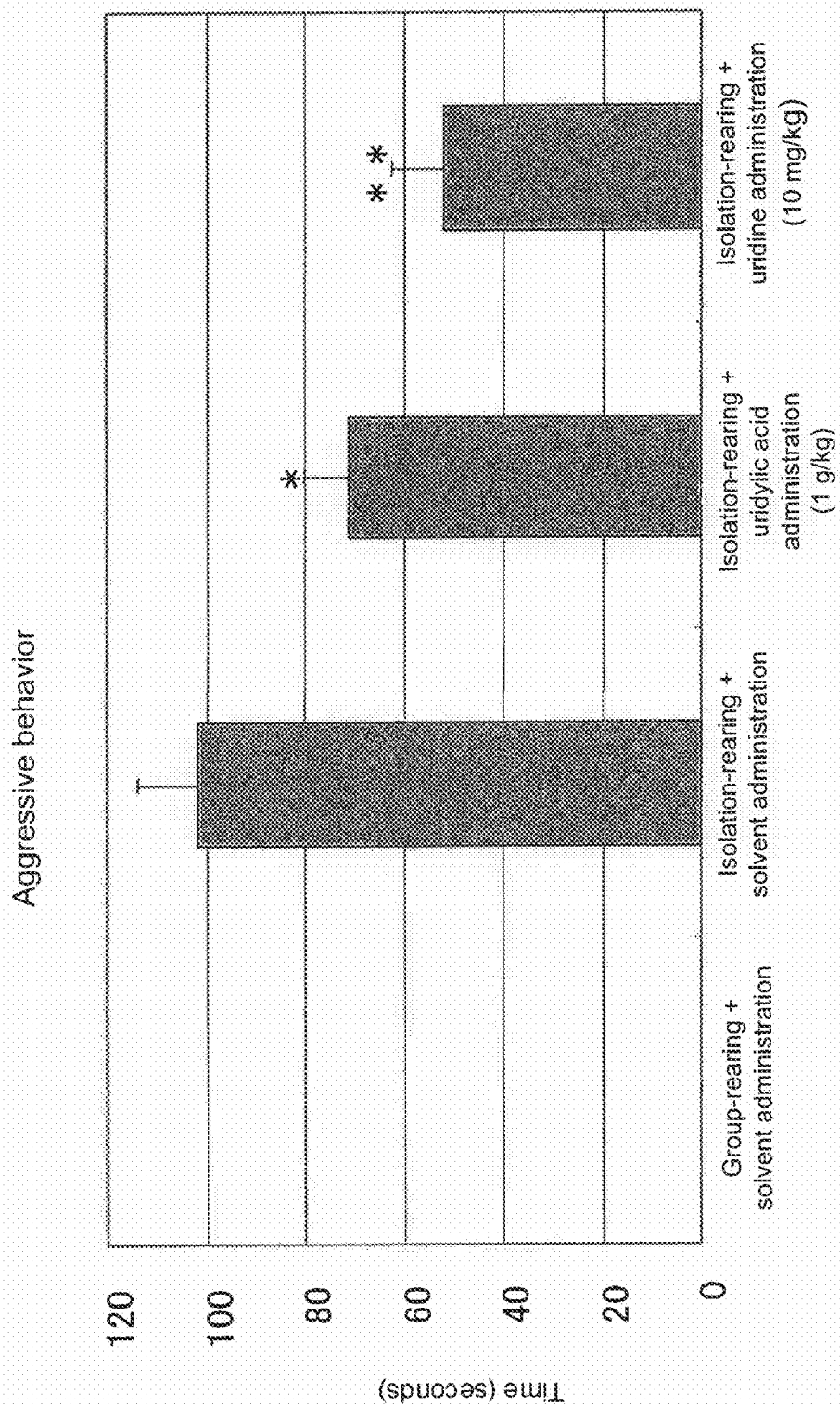

AGENT AGAINST PSYCHOSOCIAL STRESSES

CROSS-REFERENCE TO RELATED APPLICATIONS

This application is a 371 of PCT/JP07/00688 filed Jun. 26, 2007 and claims the benefit of JP 2006-177094 filed Jun. 27, 2006.

TECHNICAL FIELD

The present invention relates to an agent against psychosocial stress (hereinafter may be referred to as an "anti-psychosocial stress agent") containing, as an active ingredient, uridylic acid, uridine, or uracil.

BACKGROUND ART

Stress is psychosomatic strain caused by various external stimuli that are perceived as burdens. Examples of stress-causing factors (stressors) include physicochemical factors (e.g., cold, heat, noise, and chemical substances); biological factors (e.g., starvation, infection, fatigue, and lack of sleep); and social factors (e.g., mental tension, anxiety, fear, and excitation). In today's complicated society, people are exposed to various types of stressors, and difficulty is encountered in avoiding such stressors in daily life.

When a living body is continuously exposed to a stressor; i.e., when the living body is continuously under stressful conditions, the living body may develop a symptom such as an increase in heart rate or blood pressure, insomnia, rough skin, fatigue, arthralgia, headache, stiff shoulders, asthenopia, anorexia, or constipation. When the living body is further continuously exposed to stressors, the stressors may adversely affect organs of the whole body, resulting in, for example, severe psychosomatic disorder, peptic ulcer, cardiac disease, cerebrovascular disorder, hypertension, or hyperlipidemia.

Conceivably, effective means for coping with such stress is to take an anti-anxiety drug, a hypnotic, or a similar drug, to thereby temporarily alleviate psychosomatic reaction to stressors. However, there has not yet been known an anti-stress drug which has no side effects and can be continuously taken daily.

A benzodiazepine drug, which is a typical anti-anxiety drug, is considered to mitigate, for example, anxiety, tension, depression, or myotonia without affecting the level of consciousness, since the drug acts less directly on the cerebral limbic-neocortical system. However, as has been known, high-dose administration or continuous administration of such a drug causes a withdrawal symptom such as convulsion or delirium, or a side effect such as drowsiness, stagger, dizziness, hepatic disorder, or leukopenia.

Recently, anti-stress compositions containing, for example, a food ingredient have been reported. Specifically, there has been reported a composition containing, for example, β-carotene, L-theanine, astaxanthin, sour milk, gluten, a solvent extract of a plant belonging to the family Ebenaceae, royal jelly, or γ-aminobutyric acid (GABA). Of these substances, particularly, GABA has become of interest as an anti-stress substance (Patent Document 1 and Non-Patent Document 1).

Also, there have been reported a composition containing a plurality of nucleic-acid-related compounds and exhibiting an anti-stress effect, an anti-anxiety effect, or a depression-relieving effect; and an oxidative stress inhibitor containing, as an active ingredient, one or more species selected from among nucleic-acid-related substances including uridylic acid, uridine, and uracil (Patent Documents 3 to 5). Furthermore, there has been reported a method for the treatment of a human with neurological disorders (including stress), the method including administration of an effective dose of uridine or a uridine source (Patent Document 6).

Non-Patent Document 1: Proceedings of Annual Meeting of Japan Society for Bioscience, Biotechnology, and Agrochemistry 2006, Lecture No. 2J16p01-03, page 72
Patent Document 1: JP-A-2002-65175
Patent Document 2: JP-A-2003-327528
Patent Document 3: JP-A-1995-215879
Patent Document 4: JP-A-1998-203989
Patent Document 5: JP-A-2005-330213
Patent Document 6: JP-A-2003-517437

DISCLOSURE OF THE INVENTION

Problems to be Solved by the Invention

However, in compositions containing a plurality of nucleic-acid-related compounds to obtain an anti-stress effect, an anti-anxiety effect, or a depression-relieving effect, it has not been determined which component actually functions effectively. Moreover, no evidence has been provided that a single specific component effectively prevents or alleviates stress.

In the specification disclosing the method for the treatment of a human with neurological disorders (including stress), which method includes administration of an effective dose of uridine or a uridine source, no working examples are provided that indicate an anti-stress effect of uridine or a uridine source, and no evidence is provided to show whether or not uridine or a uridine source exhibits an anti-stress effect.

"Oxidative stress," which is targeted by an oxidative stress inhibitor, refers to stress which is caused by free radicals (i.e., active oxygen species or active nitrogen species) and is generally associated with aging or senescence (see, for example, the specification of Patent Document 5, Folia Pharmacologica Japonica, Vol. 126, No. 4, pp. 246-249 (2005), and Folia Pharmacologica Japonica, Vol. 120, No. 4, pp. 229-236 (2002)). Oxidative stress is fundamentally different, in terms of symptom or pathological condition, from "psychosocial stress," which is targeted by the present invention and is caused by change of social environment or lack of social stimuli ("Mechanism of Sleep," pp. 52-73 "Stress and Sleep," Asakura Publishing Co., Ltd. (1997)), although the term "stress" is common to both oxidative stress and psychosocial stress.

In view of the foregoing, an object of the present invention is to provide an anti-psychosocial stress composition which effectively alleviates psychosomatic symptoms under psychosocial stress conditions, and which is safe, readily available, and inexpensive.

Means for Solving the Problems

In order to achieve the aforementioned object, the present inventors have conducted extensive studies and have found that uridylic acid, uridine, or uracil, each of which is a nucleic acid component, exhibits excellent anti-psychosocial stress effect by itself. The present invention has been accomplished on the basis of this finding.

Accordingly, the present invention is directed to an anti-psychosocial stress agent containing, as an active ingredient, uridylic acid, uridine, or uracil.

The present invention also provides use of uridylic acid, uridine, or uracil for producing an anti-psychosocial stress agent.

The present invention also provides a method for mitigating, alleviating, or relieving psychosocial stress, comprising administering an effective amount of uridylic acid, uridine, or uracil to a subject in need thereof.

Effects of the Invention

The present invention has first realized provision of an anti-psychosocial stress agent containing, as an active ingredient, uridylic acid, uridine, or uracil. Since uridylic acid, uridine, or uracil, which is an active ingredient of the anti-psychosocial stress agent of the present invention, is inexpensively available and is a biological component, the agent exhibits high safety and can be continuously taken. Therefore, the anti-psychosocial stress agent of the present invention is effective for mitigating, alleviating, or relieving psychosocial stress, which is an issue in modern society. When the anti-psychosocial stress agent is taken before development of symptoms associated with psychosocial stress, the symptoms can be prevented. The anti-stress effect of the agent is superior to that of GABA, which has become of interest and has been incorporated into, for example, foods.

BRIEF DESCRIPTION OF THE DRAWINGS

FIG. 2 shows the results of an experiment in which isolation-rearing of male ddy mice was initiated at four weeks old, to thereby impose sociopsychological stress (stress caused by isolation-rearing) on the mice; and, six weeks after initiation of isolation-rearing, two mice were placed in the same cage for 20 minutes, and the time during which aggressive behavior was observed was measured (data: from left to right, group-rearing group (solvent administration), isolation-rearing group (solvent administration), isolation-rearing group (uridylic acid (1 g/kg) administration), and isolation-rearing group (uridine mg/kg) administration)).

BEST MODES FOR CARRYING OUT THE INVENTION

Figure 1:
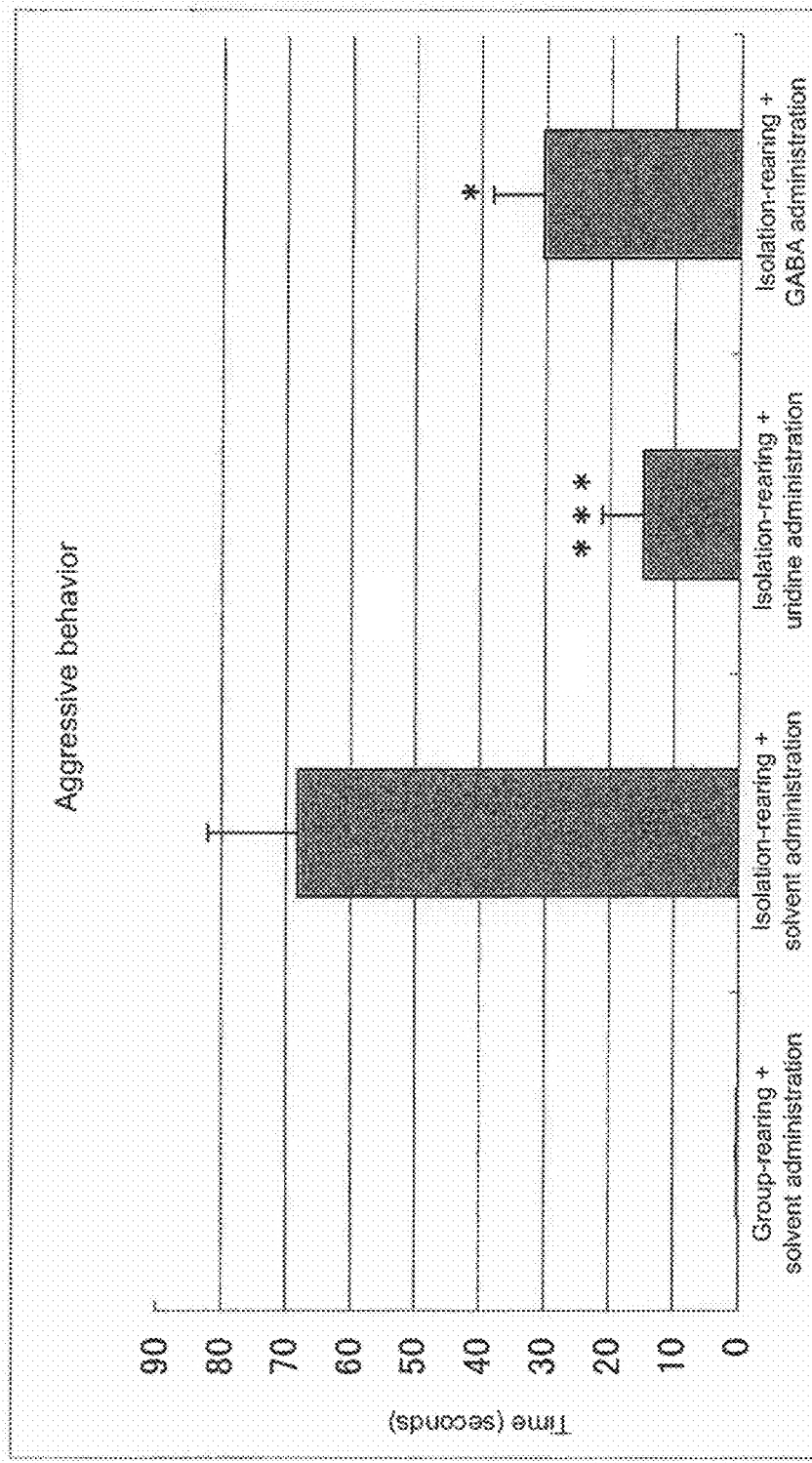
FIG. 1 shows the results of an experiment in which isolation-rearing of male ddy mice was initiated at four weeks old, to thereby impose sociopsychological stress (stress caused by isolation-rearing) on the mice; and, six weeks after initiation of isolation-rearing, two mice were placed in the same cage for 20 minutes, and the time during which aggressive behavior was observed was measured (data: from left to right, group-rearing group (solvent administration), isolation-rearing group (solvent administration), isolation-rearing group (uridine (100 mg/kg) administration), and isolation-rearing group (GABA (100 mg/kg) administration)).

As used herein, the term "psychosocial stress" refers to stress caused by change of social environment or lack of social stimuli. Examples of stress-causing factors (mental stressors) include human relationships, change of social environment (e.g., death of one's spouse, divorce, and living and working alone away from home), and lack of social stimuli. Examples of stress-related physical symptoms include increased anxiety, tension, insomnia, and startle response, increased aggression, increased endocrine response, and increased sympathetic nervous system activity ("Mechanism of Sleep," pp. 52-73 "Stress and Sleep," Asakura Publishing Co., Ltd., (1997) and "Sutoresu no Jiten" (Stress Dictionary), Chapters 1 to 3, Asakura Publishing Co., Ltd., 2005).

Psychosocial stress is also called, for example, "sociopsychological stress," "mental stress," "social and psychological stress," or "psychological stress," all of which refer to the same concept.

The anti-psychosocial stress agent of the present invention exhibits the effect of mitigating, alleviating, or eliminating the aforementioned symptoms associated with psychosocial stress. The anti-psychosocial stress agent contains uridylic acid, uridine, or uracil as an active ingredient to exhibit such an effect. Of these substances, uridylic acid or uridine (in particular, uridine) is effectively employed.

Uridylic acid, uridine, or uracil, which is employed as an active ingredient, is a compound recognized as a natural component present in living body and thus does not pose a problem in terms of safety. Particularly, uridylic acid is registered as a food additive.

No particular limitation is imposed on the origin of such an active ingredient, but the active ingredient is preferably derived from natural sources such as yeast, bacteria, fishes and shellfishes, animals, and plants.

The anti-psychosocial stress agent of the present invention, which contains such an active ingredient, may be practically employed in various types of compositions for human or non-human animals; for example, pharmaceutical products, foods and beverages, supplements, infant formula, enteral nutrients, health foods and beverages (including foods for specified health use), and animal feed additives.

When the anti-psychosocial stress agent is employed in, for example, a food or beverage, a health food or beverage, or infant formula, the active ingredient of the present invention may be employed as is, or may be employed in combination with another food or a food ingredient and prepared, through a customary method, into a composition in the form of solid, powder, granules, paste, liquid, or suspension.

When the anti-psychosocial stress agent is employed in, for example, a pharmaceutical product, a supplement, an enteral nutrient, or a health food or beverage, the active ingredient of the present invention may be mixed with a pharmaceutical additive (e.g., an excipient, a binder, a disintegrating agent, a lubricant, a sweetening/flavoring agent, a dissolution aid, a suspending agent, or a coating agent), and the mixture may be prepared, through a customary method, into a composition in the form of, for example, tablet, capsule, granules, powder, syrup, or injection.

The amount of the active ingredient incorporated may be appropriately determined so as to fall within a range of 0.1 to 30% (W/W) in consideration of, for example, the purpose of use of the active ingredient (prevention of symptoms, health maintenance, or alleviation of symptoms), the age of a subject in need thereof, the method of administration or intake thereof, or the dosage form thereof.

No particular limitation is imposed on the method of administration or intake of the active ingredient, but preferably, the active ingredient is orally administered. The dose or intake of the active ingredient varies depending on, for example, the age, body weight, or degree of symptoms of a subject in need thereof, or the method of administration or intake thereof. However, the daily dose (intake) of the active ingredient may be appropriately determined to fall within a range of about 1 mg to about 800 g so that the active ingredient exhibits an anti-psychosocial stress effect.

More specifically, for example, in the case of oral intake of uridine, when the daily intake is 1 mg/kg or more (preferably about 10 to about 1,000 mg/kg), the active ingredient is envisaged to exhibit an anti-psychosocial stress effect, to thereby alleviate or ameliorate stress-related symptoms. In the case of oral intake of uridylic acid, when the daily intake is 10 mg/kg or more (preferably about 0.1 to about 10 g/kg), the active ingredient is envisaged to exhibit an anti-psychosocial stress effect, to thereby alleviate or ameliorate stress-related symptoms.

Since the active ingredient of the present invention is very safe, intake in a somewhat excessive amount would cause no problem at all.

EXAMPLES

The present invention will next be described in detail by way of examples, which should not be construed as limiting the invention thereto.

Example 1

1. Preparation of Animal Model for Evaluation

When rodents are isolation-reared (one animal/cage) for a long period of time, the animals exhibit increased startle response, increased aggression, and increased endocrine response and sympathetic nervous system activity, which are not observed in rodents reared under normal conditions (i.e., group-reared rodents) (8 to 10 animals/cage). Conceivably, this phenomenon is attributed to the fact that rearing of experimental animals under conditions where social environmental change or social stimuli are absent imposes a kind of sociopsychological stress on the animals ("Mechanism of Sleep," pp. 52-73 "Stress and Sleep," Asakura Publishing Co., Ltd. (1997)). In Example 1, anti-stress effects of uridine and GABA (i.e., control) were evaluated through use of this phenomenon. Specifically, isolation-rearing of male ddy mice was initiated at four weeks old, to thereby impose sociopsychological stress (stress caused by isolation-rearing) on the mice. Thus, animal models for evaluation were prepared.

2. Evaluation Method

Matsumoto, et al. have reported that isolation-reared stress mouse models exhibit prolonged aggressiveness as the length of an isolation-rearing period is prolonged ("Mechanism of Sleep," pp. 52-73 "Stress and Sleep," Asakura Publishing Co., Ltd. (1997)). On the basis of this report, the following evaluation was carried out. Specifically, six weeks after initiation of isolation-rearing, two mice were placed in the same cage for 20 minutes, and the time during which aggressive behavior was observed was measured. The effect of uridine or GABA on prolongation of aggressive behavior was evaluated.

3. Administration of Compound

A test compound was suspended or dissolved in 0.5% aqueous carboxymethylcellulose solution, and the resultant suspension or solution was orally administered once a day, six days a week, until the end of the experiment.

Mice were divided into four groups. Mice of one group were group-reared and received a solvent. Mice of the other three groups were isolation-reared and received a solvent (100 mg/kg/day), uridine (100 mg/kg/day), and GABA (100 mg/kg/day), respectively. Observation of aggressive behavior was carried out in 17 pairs of mice in each group (n=9).
(Results)

As shown in FIG. 1, aggressive behavior was not observed in mice of the group-rearing group (i.e., mice reared under normal conditions), but aggressive behavior was considerably increased in mice of the isolation-rearing groups (i.e., sociopsychological-stress-imposed mice). However, in the uridine administration group, such aggressive behavior was found to be significantly reduced (***: $P<0.001$). In the GABA administration group (control), aggressive behavior was also found to be significantly reduced (*: $P<0.05$), but the effect in the GABA administration group was lower than that in the uridine administration group. These data indicate that the active ingredient of the present invention exhibits an anti-stress effect superior to that of GABA.

Example 2

The experiment of Example 1 was repeated, except that the dose of uridine was changed to 10 mg/kg/day, and uridylic acid was administered in place of GABA at a dose of 1 g/kg/day. As a result, as shown in FIG. 2, aggressive behavior was found to be significantly reduced in both the low-dose uridine administration group (**: $P<0.01$) and the uridylic acid administration group (*: $P<0.05$).

The invention claimed is:

1. A method for mitigating, alleviating, or relieving psychosocial stress caused by a change in social environment or lack of social stimuli, comprising administering an effective amount of uridylic acid, uridine, or uracil to a subject in need thereof.

2. The method of claim 1, comprising administering an effective amount of uridylic acid.

3. The method of claim 1, comprising administering an effective amount of uridine.

4. The method of claim 1, comprising administering an effective amount of uracil.

5. The method of claim 1, wherein the psychosocial stress is caused by a change of social environment.

6. The method of claim 1, wherein the psychosocial stress is caused by lack of social stimuli.

* * * * *